United States Patent
Han et al.

(10) Patent No.: US 9,913,880 B2
(45) Date of Patent: Mar. 13, 2018

(54) METHOD OF TREATING SEPSIS OR SEPTIC SHOCK

(75) Inventors: Myung Kwan Han, Jeonju-si (KR); Chae Hwa Yoo, Jeonju-si (KR); Eun Kyung Song, Jeonju-si (KR); Seung Ok Lee, Jeonju-si (KR)

(73) Assignee: STEMDR INC. (KR)

( * ) Notice: Subject to any disclaimer, the term of this patent is extended or adjusted under 35 U.S.C. 154(b) by 115 days.

(21) Appl. No.: 13/818,847

(22) PCT Filed: Feb. 17, 2012

(86) PCT No.: PCT/KR2012/001225
§ 371 (c)(1),
(2), (4) Date: Feb. 25, 2013

(87) PCT Pub. No.: WO2012/112007
PCT Pub. Date: Aug. 23, 2012

(65) Prior Publication Data
US 2013/0150555 A1    Jun. 13, 2013

(30) Foreign Application Priority Data

Feb. 18, 2011   (KR) .................. 10-2011-0014474
Feb. 17, 2012   (KR) .................. 10-2012-0016524

(51) Int. Cl.
*A61K 38/21*    (2006.01)

(52) U.S. Cl.
CPC .................. *A61K 38/215* (2013.01)

(58) Field of Classification Search
CPC .................................................. A61K 38/215
See application file for complete search history.

(56) References Cited

FOREIGN PATENT DOCUMENTS

| | | |
|---|---|---|
| JP | H03-501382 | 3/1991 |
| JP | 2004-531546 | 10/2004 |
| JP | 2010-184929 | 8/2010 |

OTHER PUBLICATIONS

Weighardt, H., et al. Type I IFN modulates host defense and late hyperinflammation in septic peritonitis. Journal of Immunology, 2006, vol. 177, p. 5623-5630.*
Durelli L, et al. Every-other-day interferon beta-1b versus once-weekly interferon beta-1a for multiple sclerosis: results of a 2-year prospective randomized multicenter study (INCOMIN). Lancet, 2002, vol. 359, p. 1453-1460.*
Li X-J, et al. Dual role of leukotriene B4 receptor type 1 in experimental sepsis. Journal of Surgical Research, 2015, vol. 193, p. 902-908.*
Nemzek, J.A. et al. Modeling sepsis in the laboratory: merging sound science with animal well-being. Comparative Medicine, 2008, vol. 58, No. 2, p. 120-128.*
Tie Fu Liu et al, NAD+ -dependent SIRT1 Deacetylase Participates in Epigenetic Reprogramming . . . , Journal of Biological Chemistry, Mar. 18, 2011, vol. 286, No. 11, pp. 9856-9864.
Hye-Sook Kwon et al, The ups and downs of SIRT1, Trends in Biochemical Sciences, 2008, vol. 33, No. 11, pp. 517-525.
Han Dai et al, SIRT1 Activation by Small Molecules, Journal of Biological Chemistry, Oct. 22, 2010, vol. 285, No. 43, pp. 32695-32703.
Jill C. Milne et al, Small molecule activators of SIRT1 as therapeutics for the treatment of type 2 diabetes, Nature, Nov. 29, 2007, pp. 712-715, 2007 Nature Publishing Group.
International Search Report for PCT/KR2012/001225 dated Sep. 12, 2012 from Korean Intellectual Property Office.
Akihiro Matsukawa, et al., Endogenous Monocyte Chemoattractant Protein-1 (MCP-1) Protects Mice in a Model of Acute Septic Peritonitis: Cross-Talk Between MCP-1 and Leukotriene B4; J Immunol 1999; 163:6148-6154; http://www.jimmunol.org/content/163/11/6148.
Official Action for Japan Patent Application No. 2016-219996, dated Aug. 9, 2017, 3 pages.

* cited by examiner

*Primary Examiner* — Robert S. Landsman
*Assistant Examiner* — Bruce D. Hissong
(74) *Attorney, Agent, or Firm* — Sheridan Ross P.C.

(57) ABSTRACT

The present invention relates to a composition containing an inducer of SIRT1 (silent mating type information regulation 2 homolog) expression for preventing or treating sepsis or septic shock. The inducer of SIRT1 expression can remarkably reduce the mortality caused by sepsis or septic shock by reducing pro-inflammatory cytokines and increasing anti-inflammatory cytokines. Therefore, the inducer of SIRT1 expression is useful for preventing or treating sepsis or septic shock.

9 Claims, 4 Drawing Sheets

METHOD OF TREATING SEPSIS OR SEPTIC SHOCK

TECHNICAL FIELD

The present invention relates to a composition containing an inducer of SIRT1 (silent mating type information regulation 2 homolog) expression for preventing or treating a sepsis or septic shock.

BACKGROUND ART

Bacterial infections and other strong stimuli may initiate an immune reaction which may cause a systemic inflammation or a systemic inflammatory response system (SIRS). A serious SIRS causes serious fever, hypotoxemia, trachypnea, tachycardia, endothelium inflammation, myocardial dysfunction, mental disorder, blood vessel collapse, and eventually a multiple organ failure syndrome (MODS) which accompanies an organ injury, e.g., an acute respiratory distress syndrome, coagulation disorder, heart failure, renal failure, shock and/or coma.

A sepsis is defined as a situation in which an infection has been confirmed or is doubted along with a systemic inflammatory response. A sever sepsis is defined as a case in which a sepsis is accompanied by an organ dysfunction (low blood pressure, hypoxia, oliguria, metabolic acidosis, thrombocytopenia, consciousness disorder). A septic shock is defined as a case in which blood pressure is not normalized even if infusion therapy is used or medicine for enhancing blood pressure is used. The sepsis may progress to a severe sepsis and finally a clinical step of a septic shock. The clinical sepsis is defined in a broad sense as a state in which the invasion by the microorganism agent is related with the clinical symbols of the infection. The clinical symbols of the sepsis are (1) Body temperature >38° C. or <36° C.; (2) Heart rate >90 times per minute; (3) Respiratory rate >20 times per minute or $PaCO_2$<32 mmHg; (4) The number of white corpuscles >12000/cu mm, <4,000/cu mm or >10% immature (band) form; (5) organ dysfunction or high blood pressure, but the present invention is not limited to these examples.

If an infection occurs, the macrophage of the infection region is activated so as to secrete TNF-α and IL-1, thereby the amount of discharge of the plasma protein into the organs increases, the movement of phagocytes and lymphocytes to the organs increases, and the attachment of the blood platelets on the walls of the blood vessels increases. In this way, the local blood vessels are closed, and the pathogenic organisms are concentrated on the infected region. Particularly, in the sepsis, the systemic infection occurs, and the serious blood vessel closure induced by TNF-α is accompanied. Further, the systemic discharge of TNF-α causes the loss of the volume of the blood plasma due to the blood vessel enlargement and the increase of the permeability of the blood vessel, thereby causing a shock. In the septic shock, TNF-α further stimulates blood coagulation, thereby causing generation of blood clots and mass consumption of blood coagulation protein in small blood vessels. Since the blood coagulation ability of a patient is lost, important organs such as kidney, liver, heart, and lung are damaged by the dysfunction of the normal vessels. It has been reported that the mortalities of the severe sepsis and the septic shock reach 25 to 30% and 40 to 70%, respectively.

In many cases of the sepsis, the pathogenic organism is *E. coli*, but gram negative bacteria such as *Klebsiella-Enterobacter-Serratia* group and *Pseudomonas* may also cause such a state. Gram-positive microorganisms such as *Staphylococcus*, systemic viruses and Fungus may also cause the sepsis.

Urogenital vessel, gastrointestinal vessel and respiratory tract are most commonly infected regions which cause the sepsis. In addition, other sepsis-related infection regions are a cut or burn region, a pelvic infection region and a catheter infection region within a vein, etc.

The sepsis mostly frequently occurs in a hospitalized patient suffering from a basal disease or symptom sensitive to the invasion of the hematocele, or a burn, wound or surgical patient. Factors of making a person sensitive to the invasion of the hematocele are a weakened immune system, for example, an immune system of an infant or an elderly person, and a symbol or disease which increases a local sensitivity to infection, for example, a weakened circulation, diabetes, uremia and AIDS. Finally, a subject having a tendency of a weakened immune response which may occur due to the existence of various allelic genes of IL-1 gene also has a greater possibility of an outbreak of the sepsis (U.S. Pat. No. 6,251,598).

It is understood that the sepsis is generated as a result of complicated reciprocal action between bacteria causing infection and the immune, inflammation and coagulation system of the host. Both the response level of the host and the features of the bacteria causing infection significantly affect the convalescence of the sepsis. Organ failure observed in the sepsis occurs when the response to the bacteria causing the infection of the host is inappropriate, and if the response is excessively increased, the organ of the host itself may be damaged. Based on this concept, antagonists to TNF-α, IL-1β, IL-6, which are proinflammatory cytokines that perform a leading role in the inflammation response to the host, has been used in an attempt to cure the sepsis, but most of the attempts have failed, and injection of activated protein C and treatment of glucocorticoid are now being used in an attempt to cure the sepsis, but many limits are being indicated. Hence, there is a need for a new treatment for preventing or treating the sepsis and the septic shock.

SIRT1 (silent mating type information regulation 2 homolog; sirtuin 1) is known as an enzyme for regulating the function of the protein by deacetylating the lysine residue of various proteins, which depends on NAD+ (Ageing Res, Vol. 1, pages 313-326, (2002)), and is most similar to Sir2 of the yeast having (NAD+)-dependent class III histone deacetyl activity. In particularly, SIRT1 cuts the acetyl group attached on the transcription factor such as Nuclear factor-kB and p53 (Cancer Res, Vol. 64, pages 7513-7525, (2004); Cell, Vol. 107, pages 149-159, (2001); Trends Endocrinol Metab, Vol. 17, pages 186-191, (2006)). Further, SIRT1 participates in reconfiguration of chromatin related with the inhibition of gene expression, DNA damage response, life extension related with restricted diet, etc. (Chen et al., Science 310, 1641, 2005). That is, SIRT1 reconfigures chromatin through histone deacetylation as in Sir2 of the yeast, inhibits expression of gene, and induces deacetylation of various transcription factors related with cell growth, stress reaction and internal secretion regulation, etc. as well as histone protein. Further, according to a recent study, there has been a report of a technology which applies the SIRT1 to diabetes, obesity, nervous degenerative diseases or aging related diseases, etc. by increasing the deacetylation of the SIRT1.

Likewise, there is a report on pharmacological effects that the SIRT1 may be applicable to various diseases by increasing the deacetylation activity, but there is no study on pharmacological effects for preventing or treating the sepsis or septic shock. Hence, there is a need for a new treatment for preventing or treating the sepsis or septic shock.

DISCLOSURE

Technical Problem

The inventors of the present invention have been developing a new treatment of a sepsis or a septic shock, and have found that SIRT1 expression inducer may significantly reduce the mortality by the sepsis by reducing pro-inflammatory cytokines and increasing anti-inflammatory cytokines.

Hence, an object of the present invention devised to solve the problem lies in providing a composition containing an inducer of SIRT1 (silent mating type information regulation 2 homolog) expression for preventing or treating sepsis or septic shock.

Technical Solution

The present invention provides a composition containing an inducer of SIRT1 (silent mating type information regulation 2 homolog) expression for preventing or treating sepsis or septic shock.

Further, the present invention provides a composition containing an inducer of SIRT1 (silent mating type information regulation 2 homolog) expression for preventing or improving sepsis or septic shock.

Advantageous Effects

According to the present invention, SIRT1 expression inducer may significantly reduce the mortality by the sepsis by reducing pro-inflammatory cytokines and increasing anti-inflammatory cytokines, and thus may be utilized in preventing or treating a sepsis or a septic shock.

BEST MODE

Figure 1:
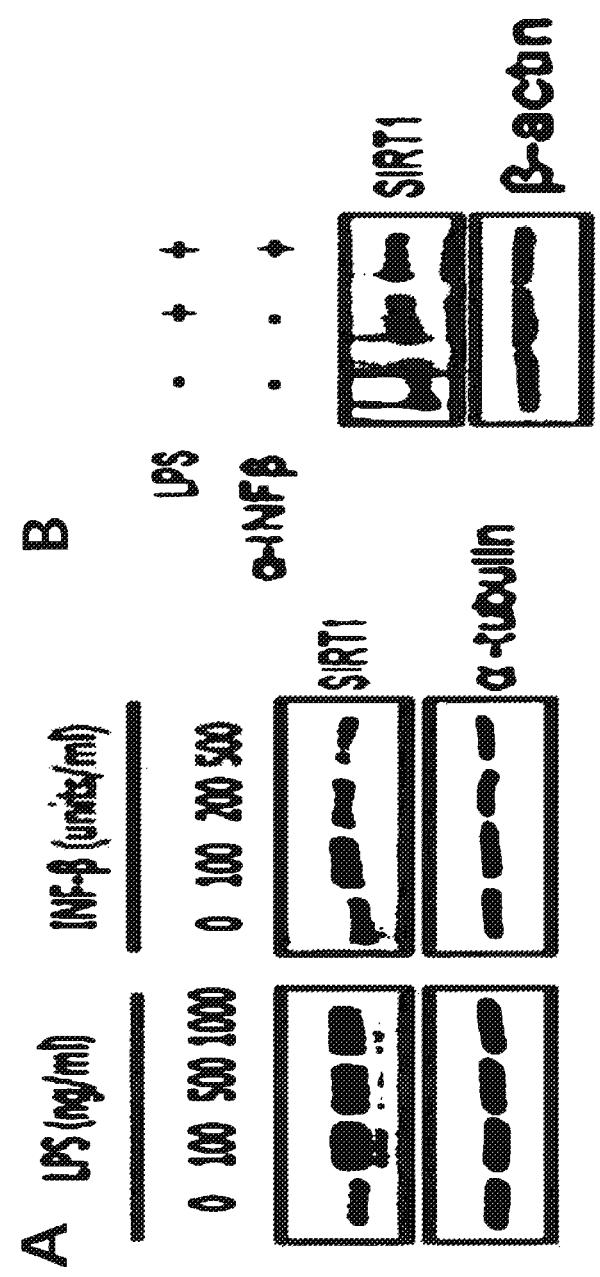
FIG. 1 shows a result of analysis of SIRT protein expression by western blot after (A) treatment of LPS and interferon beta and (B) treatment of IFN-β blocking antibody (a-INF β) and LPS to a macrophage originated from the marrow of a mouse.

The present invention provides a composition containing an inducer of SIRT1 (silent mating type information regulation 2 homolog) expression for preventing or treating sepsis or septic shock.

The composition includes a pharmaceutical composition and food composition.

Hereinafter, the present invention will be described in detail.

According to the present invention, SIRT1 expression inducer may significantly reduce the mortality by the sepsis by reducing pro-inflammatory cytokines and increasing anti-inflammatory cytokines, and thus may be utilized in preventing or treating a sepsis or a septic shock.

The SIRT expression inducing material may include at least one selected from a group composed of an interferon beta, cyclic guanosine monophosphate (cGMP), adiponectin, pyruvate, and 2-deoxyglucose, but the present invention is not limited thereto.

The interferon beta may include one of two isoforms, i.e., interferon beta 1a (IFN-β1a) and interferon beta 1b (IFN-β1b). Interferon beta 1a is produced from Chinese hamster ovary (CHO) containing human interferon beta genes, is composed of 166 amino acid residues, and is glycosylated protein having a size of 25 kD. Interferon beta 1b is protein composed of 165 amino acid residues produced from $E.\ coli$, does not have sugar, and does not have amino acid no. 1 methionine residue. Further, no. 17 cysteine residue has been substituted by serine. It is known that interferon beta 1a and interferon beta 1b may be used to treat multiple sclerosis, but it is not known that they are used to prevent or treat a sepsis or a septic shock.

The prevention or treatment of the sepsis or the septic shock means reducing, improving or removing clinical symbols related with the sepsis and the state related to the multi-organ failure syndrome, for example, fever, hypotoxemia, trachypnea, tachycardia, endothelium inflammation, myocardial dysfunction, mental disorder, blood vessel collapse, and eventually an organ injury, e.g., an acute respiratory distress syndrome, coagulation disorder, heart failure, renal failure, shock and/or coma.

The composition of the present invention may contain one of known valid elements having the effects of preventing or treating a sepsis or septic shock along with SIRT1 expression inducing materials.

The pharmaceutical composition of the present invention may include at least one of pharmaceutically allowable carriers for injection in addition to the above disclosed valid elements. Some examples of a carrier, an excipient, and a diluent are lactose, dextrose, sucrose, sorbitol, mannitol, xylitol, aerythritol, maltitol, starch, acacia gum, alginate, gelatin, calcium phosphate, calcium silicate, cellulose, methylcellulose, propylhydroxybenzoate, talc, magnesium stearate, and mineral. The pharmaceutical composition of the present invention may be prepared using a generally used a filler, an extender, a binder, a wetting agent, a disintegrant, a diluent such as a surfactant, or an excipient.

Solid content for oral dosage includes a tablet, pill, powder, granule, capsule, etc., and the solid content is prepared mixing the above valid element with at least one of the excipient such as starch, calcium carbonate, sucrose, lactose, gelatin, etc. Further, a lubricant such as magnesium stearate and talc may also be used in addition to a simple expient.

Liquid substances for oral dosage may mean a suspension, liquid, oil, syrup, etc., and may include various expients such as a wetting agent, a sweetener, an aromatic, and a preservative.

Substances for parenteral dosage include sterilized aqueous solution, suspension, non-aqueous solvent, oil, lyophiliztion materials, and suppository. Plant oil such as propylene glycol, polyethylene glycol, and olive oil, and injectable ester such as ethylolate may be used as suspend and non-aqueous solvent. Witepsol, macrogol, twin 61, cacao butter, Laurin, glycerinated gelatin, etc.

Pharmaceutical composition of the present invention may be injected in various ways according to a purposed method. For example, the composition may be injected by oral dosage, rectum, vein, muscle, hypodermic injection, intradural injection within the womb, or cerebrovascular injection.

The valid amount of injection of the pharmaceutical composition of the present invention may be different depending on the patient's state, weight, level of disease, type of composition, injection path, and period, but may also be appropriately selected by those skilled in the art. The daily amount of injection of the SIRT1 expression inducing material is preferably between 5000 and 50000 IU/kg, the amount may be injected once a day or the amount may be divided into several parts to be injected several times a day, but the injection method of the present invention is not limited to this example.

Further, the pharmaceutical composition of the present invention may be used along with an anti-inflammatory agent, antipyretic anodyne, blood coagulation inhibitor, antibiotic, bactericide, anti-allergy agent, etc.

The food composition of the present invention may additionally include a carrier allowable as food. For example, when the food composition is a drink, there is no restriction in the liquid except the fact that SIRT1 expression inducing material should be contained as an essential element, and several flavoring agents or natural carbohydrate, etc. may be contained as in common drinks. At this time, some examples of natural carbohydrate are monosaccharide such as glucose and fructose, disaccharide such as maltose and sucrose, polysaccharide such as dextrin and cyclodextrin, and sugar alcohol such as xylitol, sorbitol, and erythritol, etc. Further, some examples of the flavoring agent are natural flavoring agents such as thaumatin, stevia extracts, and glycyrrhizin, and synthetic flavoring agents such as saccharin and aspartame.

In addition to the above drinks, the food composition of the present invention may contain various medicines for promoting nutrition, vitamins, minerals, synthetic flavoring agents, natural flavoring agents, coloring agents, enhancers, pectic acids, salt thereof, alginic acids, salt thereof, organic acids, protective colloid thickeners, pH adjusters, stabilizers, preservatives, glycerin, alcohol, carbonation reagents used in soda, etc.

The food composition may be provided as various foods, candy, chocolate, gum, tea, vitamin complex, various health supplements, etc., and may be provided in the form of powder, granules, pills, capsules or drinks.

The valid amount of the SIRT1 expression inducing material contained in the food composition may be set according to the valid amount of the pharmaceutical composition, but when the food composition is taken in for a long period for the purpose of health or hygiene, or for the purpose of health adjustment, the valid amount may be less than the above amount.

DETAILED DESCRIPTION OF EXEMPLARY EMBODIMENTS

Hereinafter, exemplary embodiments of the present invention will be described in detail. However, the exemplary embodiments below merely illustrate the present invention, and the present invention is not limited to the embodiments.

Exemplary Embodiment 1: Measuring Amount of SIRT1 Expression after Treatment of LPS and Interferon to Macrophage Originated from Mouse Marrow Femur and tibia marrow cells of C57BL/6 mouse have been differentiated in culture solution containing M-CSF (10 ng/ml), and then have been used as mouse macrophage. LPS (0, 100, 500, 1000 ng/ml) and interferon beta (0, 100, 200, 500 units/ml) have been injected to the macrophage by concentrations, and the SIRT1 expression amount has been compared by western blot. Further, the SIRT1 protein expression amount when LPS has been injected along with IFN-β blocking antibody has been measured.

The result is shown in FIG. 1.

As illustrated in FIG. 1, when LPS has been injected to the macrophage originated from the mouse marrow by 100 ng/ml, the SIRT protein expression has increased most, and when 500 ng/ml and 1000 ng/ml of LPS has been used, the SIRT1 protein expression has rather decreased. Further, when interferon beta has been used by concentrations, the SIRT1 expression has most significantly increased when 100 units/ml has been used.

Further, the SIRT1 expression increased by LPS decreased again by injecting IFN-β blocking antibody together. Hence, it can be known that the secretion of the SIRT1, which has been increased by LPS, is performed through the interferon beta, and through which the interferon beta induces the expression of SIRT1 (B).

Exemplary Embodiment 2: Influence of Adenovirus-SIRT1 and Interferon Beta on the Amount of Secretion of Pro-Inflammatory and Anti-Inflammatory Cytokines After infecting the macrophage with the adenovirus-SIRT1 by 10,000 MOI (multiplicity of infection), LPS 100 ng/ml has been injected for 24 hours. Further, LPS 100 ng/ml has been used along with interferon beta 100 units/ml for 24 hours, and then the amount of secretion of pro-inflammatory and anti-inflammatory cytokines of the cell culture medium has been measured by Elisa. The experiment has been performed three times, and the result has been expressed by the average±standard deviation.

Figure 2:
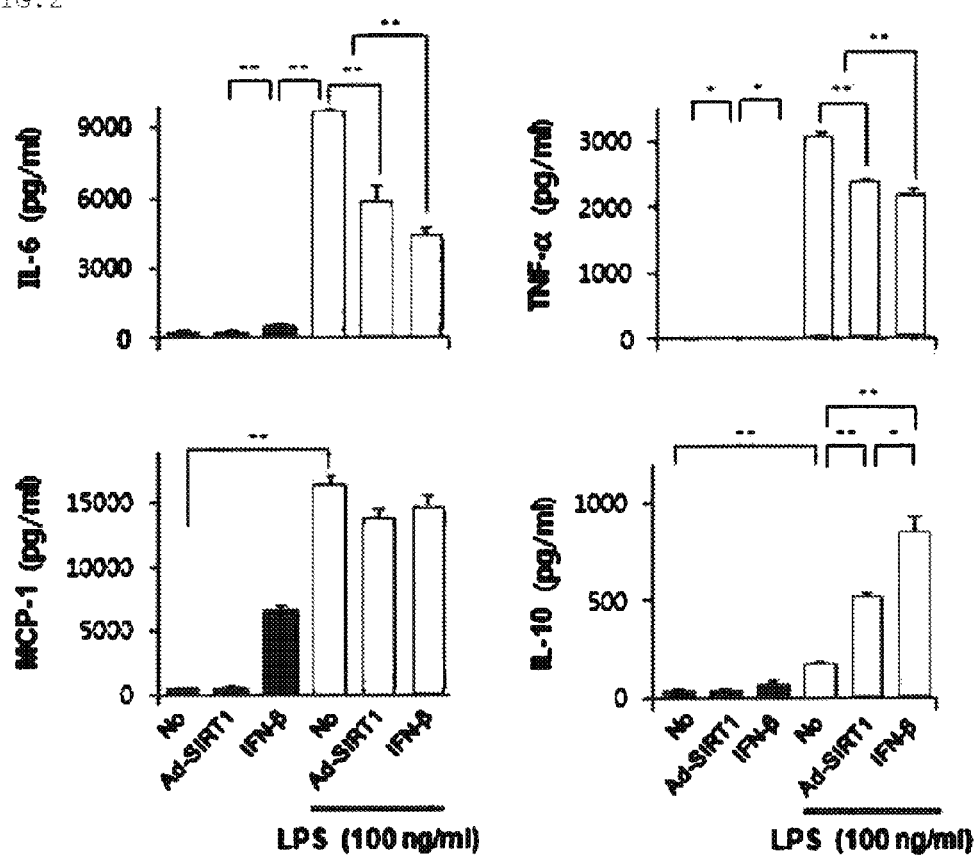
FIG. 2 shows of a result of analysis the amount of pro-inflammatory cytokines and anti-inflammatory cytokines secreted after inducing overexpression of SIRT1 using adenovirus-SIRT1 and interferon beta to the macrophage originated from the mouse marrow and processing LPS ((*, P<0.05; **, P<0.01 (Student test)).

The result is shown in FIG. 2.

As shown in FIG. 2, with respect to the amount of the pro-inflammatory cytokines, which has been increased by the LPS treatment, IL-6 has been decreased by 40% and 54%, respectively, and TNF-α has been decreased by 22% and 29%, respectively, by the pre-treatment of adenovirus-SIRT1 and interferon beta. Further, it has been found that MCP-1, which is another pro-inflammatory cytokine, which is increased by the LPS treatment, has slightly decreases by the adenovirus-SIRT1 and interferon beta. In contrast, it has been found that the amount of the IL-10, which is the anti-inflammatory cytokine, has increased by 2.8 times and 4.7 times, respectively. Hence, it is understood that the treatment by the interferon beta, which is the cytokine that promotes the expression of SIRT1, may inhibit the excessive inflammatory response by the LPS.

Exemplary Embodiment 3: Analysis of Survival Rate of Mouse after Injecting LPS after Pre-Treatment of SIRT1 or Interferon Beta to Mouse Adenovirus-LacZ, which is control gene delivery system, and adenovirus-SIRT1, which is the SIRT1 gene delivery system, are injected into the mouse tail vein by $3\times10^8$ pfu (plaque forming unit), and LPS 15~20 mg/kg after 48 hours. Then the survival rate of the mouse has been observed for 10 days.

Further, interferon beta 1000 units or the same amount of salt solution per 20 g of the mouse weight is injected into the mouse tail vein, and LPS 15-20 mg/kg has been injected after 30 minutes. Then the survival rate of the mouse has been observed for 10 days.

Figure 3:
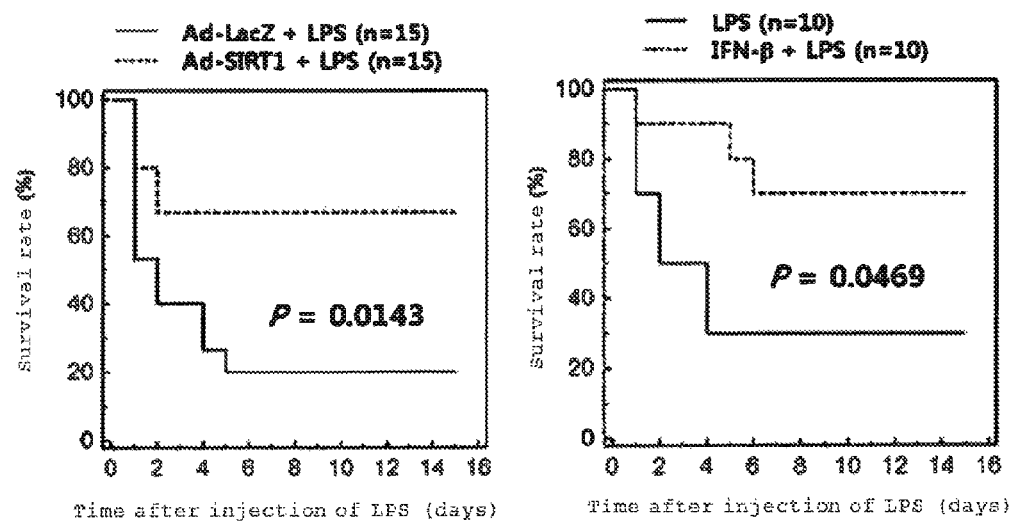
FIG. 3 shows the survival rate of the mouse after injecting LPS after pre-treatment of adenovirus-SIRT1 or interferon beta to the mouse.

The result is shown in FIG. 3.

As shown in FIG. 3, When the LPS is injected to the mouse which has been pre-injected with the adenovirus-SIRT1, the survival rate of the mouse after 10 days is 66^, and thus the survival rate has been significantly higher than the survival rate 20% of the control group, the mouse, to which the adenovirus-LacZ has been injected. Further, the survival rate of the mouse, into which the LPS has been injected after the injection of the interferon beta, was 70%, which was significantly higher than the survival rate 30% of the control group, the mouse, into which the salt solution has been injected. The result shows a significant difference even by the Kaplan-Meier survival statistical analysis ($p<0.05$). Hence, the interferon beta, which is a substance that induces the SIRT1 expression, significantly reduces the mortality of the mouse by the LPS treatment by inhibiting the excessive inflammatory response by the LPS.

Exemplary Embodiment 4: Analysis of Survival Rate of Mouse at the Time of Treatment of Adenovirus-Dominant-Negative SIRT1

Adenovirus-Dominant-negative SIRT1, which the gene delivery system for blocking the function of the intrinsic SIRT1, (Adenovirus for inducing mutant protein that has changed histidine no. 355 into tyrosine), is injected into the mouse tail vein by $3\times10^8$ pfu, and after 48 hours, interferon beta 1000 units per 20 g of the mouse weight is injected into the mouse tail vein. After 30 minutes, LPS 15-20 mg/kg is injected, and the survival rate of the mouse is observed for 10 days.

Figure 4:
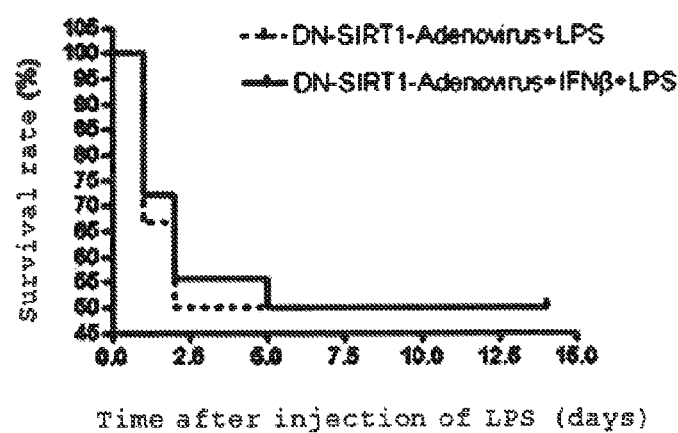
FIG. 4 shows the survival rate of the mouse after processing LPS after injecting Adenovirus-Dominant-negative SIRT1 and interferon beta to the mouse.

The result is shown in FIG. 4.

As shown in FIG. 4, in the case in which Adenovirus-Dominant-negative SIRT1 is pre-injected for 48 hours, interferon beta is injected and then LPS is injected into the mouse, the survival rate 50% has been observed after 10 days. This is a result similar to the survival rate 50% of the control group, the mouse into which the salt solution has been injected, and through which the interferon beta, which is the material for inducing the SIRT1 expression, significantly reduces the mortality of the mouse by LPS.

Exemplary Embodiment 5: Analysis of Survival Rate According to SIRT1 and Interferon Beta Treatment in a Mouse Sepsis Model In a mouse sepsis model, which is induced through cecal ligation and Puncture (CLP) surgery, the following experiment has been performed to check the survival rate changed according to the injection of SIRT1 and interferon beta.

Adenovirus-LacZ or adenovirus-SIRT1 has been injected into the mouse tail vein by $3\times10^8$ pfu. After 24 hours, the anesthetic is injected into the abdominal cavity, and the sepsis has been caused through CLP. That is, after the center of the abdomen of the mouse is cut, the appendix is exposed to the outside so that the end of the ileocecal valve is ligated by the silk suture, two holes are made using a needle, and then a certain amount of fecal materials are discharged. The appendix as well as fecal materials has been inserted again into the abdomen, then the abdomen has been stitched, and then a physiological salt solution has been injected through a hypodermic injection. After two hours of SLP operation, interferon beta 1000 units or the same amount of salt solution per 20 g of the mouse weight have been injected into the mouse tail vein.

Figure 5:
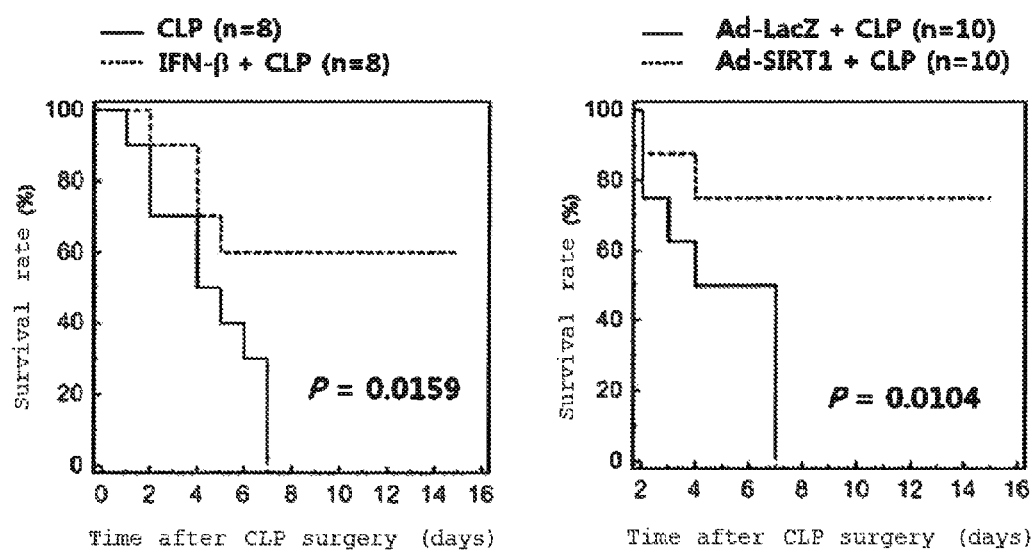
FIG. 5 shows the survival rate of the mouse after causing a sepsis by cecal ligation and Puncture (CLP) operation after treatment of adenovirus-SIRT1 or interferon beta to the mouse.

The result is shown in FIG. 5.

As shown in FIG. 5, the sepsis is induced to the mouse into which the adenovirus-SIRT1 has been injected in advance, and the survival rate of the mouse after 10 days was 60%. This is a significantly high survival rate of 0% of the control group, the mouse into which the adenovirus-LacZ has been injected in advance.

Further, in the case of the experimental group in which interferon beta has been injected into the sepsis-induced mouse, the survival rate was 76, but in the case of the control group, the mouse into which the salt solution has been injected, the survival rate was 0%. The result shows a significant difference even by Kaplan-Meier survival statistical analysis ($p<0.05$).

Hence, the interferon beta, which induces the expression of SIRT1, significantly reduces the mortality of the mouse due to the sepsis, and thus may be utilized in preventing or treating the sepsis or septic shock.

Substances for a composition of the present invention are illustrated below.

Substance Example 1: Pharmacological Substance

1. Preparation of Powder 2 g of SIRT1 expression inducing material
1 g of lactose The above materials are mixed and are then filled in an airtight container so as to make powder.

2. Preparation of a Pill 100 mg of SIRT1 expression inducing material
100 mg of corn starch
100 mg lactose
2 mg of stearic acid magnesium After mixing the above materials, pills are manufactured according to a general pill manufacturing method.

3. Preparation of Capsules 100 mg of SIRT1 expression inducing material
100 mg of corn starch
100 mg lactose
2 mg of stearic acid magnesium After mixing the above materials, capsules are prepared in gelatin capsules according to a general capsule manufacturing method.

Substance Example 2: Preparation of Food

The foods containing SIRT1 expression inducing materials of the present invention have been made as follows.

1. Preparation of Spice for Cooking

Spice for cooking for health improvement has been made as 20 to 95 weight % of SIRT1 expression inducing materials.

2. Preparation of Tomato Ketchup and Sauce 0.2 to 1.0 weight % of SIRT1 expression inducing materials has been added to tomato ketchup or sauce so as to make tomato ketchup or sauce for health improvement.

3. Preparation of Wheat Flour Food 0.5 to 5.0 weight % of SIRT1 expression inducing materials are added to wheat flour, and bread, cake, cookies, crackers and noodles are made using the mixture so as to prepare food for health improvement.

4. Preparation of Soup and Gravies 0.1 to 5.0 weight % of SIRT1 expression inducing materials are added to soups and gravies so as to prepare meat processed food, soups of noodles, and gravies for health improvement.

5. Preparation of Ground Beef 10 weight % of SIRT expression inducing materials is added to the ground beef so as to prepare the ground beef for health improvement.

6. Preparation of Diary Products 5 to 10 weight % of SIRT1 expression inducing materials is added to milk, and various diary products such as butter and ice cream are made using the milk.

Substance Example 3: Preparation of Drinks

1. Preparation of Soda 10 to 15% of SIRT expression inducing materials, 5 to 10% of sugar, 0.05 to 0.3% of citric acid, 0.005 to 0.02% of caramel, 0.1 to 1% of vitamin C and 70 to 80% of refined water are mixed to make syrup. The syrup is sterilized for 20 to 180 seconds at 85-98° C., and the syrup is mixed with the cooling water at the ratio of 1:4, then 0.5 to 0.82% of carbonic acid gas is injected so as to prepare soda containing SIRT1 expression inducing materials.

2. Preparation of Healthy Drinks

SIRT1 expression inducing materials (solid content 2.5%, 97.16%), jujube extract (65 brix, 2.67%), fruit and vegetable extract (solid content 70%, 0.12%), vitamin C (0.02%), calcium pantothenate (0.02%), licorice extract (solid content 65%, 0.01%) are mixed, then the mixture is sterilized for a few seconds, and then the mixture is packed in a small container such as a glass bottle and a plastic bottle so as to make a healthy drink.

3. Preparation of Vegetable Juice 0.5 g of SIRT1 expression inducing materials is added to 1,00 ml of tomato or carrot juice so as to make a vegetable juice for health improvement.

4. Preparation of Fruit Juice 0.1 g of SIRT1 expression inducing materials is added to 1,000 ml of apple or grape juice so as to make a fruit juice for health improvement.

The invention claimed is:

1. A method for treating a sepsis or a septic shock in a patient, the method comprising: reducing a pro-inflammatory cytokine and increasing an anti-inflammatory cytokine in the patient by administering a therapeutically effective dose of interferon beta (IFN-β), wherein the dose of IFN-β induces expression of silent mating type information regulation 2 homolog (SIRT1) as an active ingredient to the patient.

2. The method of claim 1, wherein the interferon beta is interferon beta 1 a or interferon beta 1 b.

3. The method of claim 1, wherein the dose is in an amount between 5000 and 50000 IU/kg per day.

4. The method of claim 1, wherein the pro-inflammatory cytokine is IL-6 (interleukin 6).

5. The method of claim 1, wherein the pro-inflammatory cytokine is TNF-a (tumor necrosis factor alpha).

6. The method of claim 1, wherein the anti-inflammatory cytokine is IL-10 (interleukin 10).

7. The method of claim 1, further comprising reducing at least two different pro-inflammatory cytokines, including both IL-6 (interleukin 6) and TNF-a (tumor necrosis factor alpha).

8. The method of claim 7, wherein the anti-inflammatory cytokine is IL-10 (interleukin 10).

9. A method for treating a sepsis or a septic shock in a patient, the method comprising;
reducing pro-inflammatory cytokines IL-6 (interleukin 6) and TNF-a (tumor necrosis factor alpha), and
increasing anti-inflammatory cytokine IL-10 (interleukin 10) in the patient by administering interferon beta inducing expression of SIRT1 as an active ingredient to the patient in an amount between 5000 and 50000 IU/kg per day.

* * * * *